(12) United States Patent
Dhuper et al.

(10) Patent No.: US 7,743,764 B2
(45) Date of Patent: Jun. 29, 2010

(54) AEROSOL INHALATION SYSTEMS AND INTERFACE ELEMENTS FOR USE THEREIN

(76) Inventors: Sunil Kumar Dhuper, 47 Red Ground Rd., Old Westbury, NY (US) 11568; Herbert Fred D'Alo, 37 Forest Hills Dr., Madison, CT (US) 06443; Sarita Dhuper, 47 Red Ground Rd., Old Westbury, NY (US) 11568

( * ) Notice: Subject to any disclaimer, the term of this patent is extended or adjusted under 35 U.S.C. 154(b) by 911 days.

(21) Appl. No.: 11/535,596

(22) Filed: Sep. 27, 2006

(65) Prior Publication Data

US 2007/0068516 A1  Mar. 29, 2007

Related U.S. Application Data

(63) Continuation of application No. PCT/US2005/010274, filed on Mar. 29, 2005, which is a continuation of application No. 10/812,618, filed on Mar. 30, 2004, now abandoned.

(51) Int. Cl.
A61M 11/00 (2006.01)
(52) U.S. Cl. .............. 128/200.14; 128/200.22
(58) Field of Classification Search ............ 128/200.14, 128/200.21, 200.22, 203.12, 203.13, 203.15, 128/203.16, 203.18, 203.22, 203.24, 204.18, 128/205.24
See application file for complete search history.

(56) References Cited

U.S. PATENT DOCUMENTS

| | | | |
|---|---|---|---|
| 3,057,347 A | 10/1962 | McGee | |
| 4,463,755 A | 8/1984 | Suzuki | |
| 5,263,485 A | 11/1993 | Hickey | |
| 5,287,849 A | 2/1994 | Piper et al. | |
| 5,349,946 A | 9/1994 | McComb | |
| 5,388,571 A | 2/1995 | Roberts et al. | |
| 5,482,031 A | 1/1996 | Lambert | |
| 5,640,951 A | 6/1997 | Huddart et al. | |
| 5,791,340 A | 8/1998 | Schleufe et al. | 128/203.28 |
| 5,813,423 A | 9/1998 | Kirchgeorg | |
| 5,848,587 A | 12/1998 | King | 128/200.18 |
| 5,865,172 A | 2/1999 | Butler et al. | 128/203.12 |
| 6,039,042 A | 3/2000 | Sladek | |
| 6,041,777 A | 3/2000 | Faithfull et al. | |
| 6,078,730 A | 6/2000 | Huddart et al. | |
| 6,192,884 B1 | 2/2001 | Vann et al. | |
| 6,427,685 B1 | 8/2002 | Ray | |
| 6,494,202 B2 | 12/2002 | Farmer | 128/200.23 |

(Continued)

*Primary Examiner*—Steven O Douglas
(74) *Attorney, Agent, or Firm*—Leason Ellis LLP

(57) ABSTRACT

According to one aspect of the present invention, an aerosol inhalation system including an accessory is defined by a first conduit member for delivering medication in the form of aerosol particles to a patient, as well as a first holding chamber for holding the aerosol particles prior to deliver to the first conduit member. The accessory includes a valve mechanism associated with the first conduit member and including a first valve assembly and a second valve assembly. The aerosol inhalation system includes at least one device in fluid communication with the first holding chamber for producing the aerosol particles. For example, the device can be either an MDI, a nebulizer or both devices can be used simultaneously. According to one exemplary embodiment of the present invention, the aerosol inhalation system is a closed system and is therefore capable of delivering a fixed concentration of the medication to the patient, thereby overcoming the above deficiencies that are associated with the prior art devices.

30 Claims, 9 Drawing Sheets

U.S. PATENT DOCUMENTS

| | | |
|---|---|---|
| 6,550,476 B1 | 4/2003 | Ryder |
| 6,622,725 B1 | 9/2003 | Fisher et al. |
| 6,776,160 B2 * | 8/2004 | Wang .................... 128/205.13 |
| 6,799,423 B2 | 10/2004 | Piekarski |
| 6,976,488 B2 | 12/2005 | Halperin |
| 2002/0017302 A1 | 2/2002 | Fukunaga et al. |
| 2003/0010336 A1 | 1/2003 | Vito |
| 2003/0209246 A1 | 11/2003 | Schroeder et al. |
| 2004/0011364 A1 | 1/2004 | Dhuper et al. |
| 2004/0024372 A1 | 2/2004 | Grogan |
| 2004/0123974 A1 | 7/2004 | Marler et al. |
| 2005/0092325 A1 | 5/2005 | Dionne |

* cited by examiner

AEROSOL INHALATION SYSTEMS AND INTERFACE ELEMENTS FOR USE THEREIN

CROSS-REFERENCE TO RELATED APPLICATION

The present application claims priority to U.S. patent application Ser. No. 10/812,618, filed Mar. 30, 2004, which is hereby incorporated by reference in its entirety.

TECHNICAL FIELD

The present invention relates to inhalation equipment and more particularly, relates to aerosol inhalation systems including an interface (interface element) for use in the system between a conventional part of the inhalation equipment, such as a generator, and the patient to provide, in a number of applications, a completely closed system that ensures that while the medication delivered to the patient has a fixed concentration over time, the concentration of the delivery gas remains constant throughout the delivery period.

BACKGROUND

Aerosol inhalation equipment is commonly used as a means to deliver medication in an aerosolized form to a patient. Aerosolized medication is typically used to treat patients with respiratory conditions, such as asthma or chronic obstructive pulmonary disease (COPD). For example, inhalation equipment is a common means for delivering medication to counter certain aliments of a patient population, including reactive airway disease, asthma, cystic fibrosis, etc.

It is generally accepted that effective administration of medication as aerosol depends on the delivery system and its position in relation to the patient. Aerosol particle deposition is influenced by particle size, ventilatory pattern, and airway architecture and effective medication response is also influenced by the dose of the medication used.

An aerosol delivery system includes three principal elements, namely a generator, a power source, and an interface. Generators include small volume nebulizers (SVN), large volume nebulizers (LVN), metered dose inhalers (MDI), and dry powder inhalers (DPI). The power source is the mechanism by which the generator operates or is actuated and includes compressed gas for SVN and LVN and self-contained propellants for MDI. The interface is the conduit between the generator and the patient and includes spacer devices/accessory devices with mouthpieces or face masks. Depending on the patient's age (ability) and coordination, various interfaces are used in conjunction with SVN and MDI in order to optimize drug delivery.

A SVN is a jet nebulizer that is powered by a compressed gas source. The medication is displaced up a capillary tube from the nebulizer's reservoir and is dispersed continuously as aerosolized particles. The aerosolized particles are spontaneously inhaled by the patient or delivered in conjunction with positive-pressure breaths. Typically, for patients greater than 3 years who are spontaneously breathing without an artificial airway and are able to cooperate, a mouthpiece with an extension reservoir should be used. For patients unable to negotiate a mouthpiece, typically children under 3 years, a face mask should be used.

An MDI is essentially a pressurized canister that contains a medication and propellant. Actuation of the MDI results in the ejection of one dose of medication as aerosolized particles, which can be spontaneously inhaled by the patient or delivered in conjunction with positive-pressure breaths. A spacer device/accessory device should be used with an MDI. A spacer device enhances delivery by decreasing the velocity of the particles and reducing the number of large particles. A spacer device with a one-way valve, i.e., holding chamber, eliminates the need for the patient to coordinate actuation and inhalation and optimizes drug delivery. A spacer device without valves requires coordination between inhalation and actuation. The MDI with spacer device and face mask is appropriate for patients, typically less than 3 years, unable to use a mouthpiece.

A DPI is a breath-actuated device that uses a gelatin capsule containing a single dose of medication and a carrier substance to aid in the dispersion of the drug. The capsule is inserted into the device and punctured. The patient's inspiratory flow disperses the dry particles and draws them into the lower airways. In spontaneously breathing patients, this device is appropriate in patients who are able to achieve a certain inspiratory flow, such as equal to or greater than 50 L/min. This will typically correspond to children about 6 years or greater.

A LVN can be used to deliver a dose of medication continuously over a period of time. A LVN is powered by a compressed gas source, and a face mask is typically used as the interface.

The two primary means for delivering aerosolized medication to treat a medical condition is an MDI or a nebulizer. MDI medication (drug) canisters are typically sold by manufacturers with a boot that includes a nozzle, an actuator, and a mouthpiece. Patients can self-administer the MDI medication using the boot alone but the majority of patients have difficulty in synchronizing the actuation of the MDI canister and patient inhalation and improve the delivery and improve the delivery of medication by decreasing oropharyngeal deposition of the aerosol drug.

Many valved chambers of this type are commercially available. Examples of such spacers include but are not limited to those structures disclosed in U.S. Pat. Nos. 4,470,412; 5,012,803; 5,385,140; 4,637,528; 4,641,644; 4,953,545; and U.S. patent application publication No. 2002/0129814. These devices are expensive and may be suitable for chronic conditions that require frequent use of MDI inhalers provided the cost and labor involved in frequent delivery of medication is acceptable to the patient. However, under acute symptoms, such devices may fail to serve the purpose and lead to an inadequate delivery of medication.

Aerosol delivery systems that use standard small volume nebulizers are commonly used in acute conditions as they are cheap and overcome the inhalation difficulties associated with actuation of MDI and synchronization of inhalation by the patient. Nebulizers are fraught with numerous problems as well. The medication does used is about 10 times of that used with an MDI and hence the increased cost without any added proven clinical benefit. Secondly, the majority of the nebulized medication is wasted during exhalation. Thirdly, the time taken to deliver the medication is several times that of an MDI and the labor cost of respiratory therapist may outweigh the benefits of nebulizers compared with MDIs. Breath actuated nebulizers(s) with reservoir have been designed to overcome the medication waste. An example of this type of device is found in U.S. Pat. No. 5,752,502. However, these devices are expensive and still have all the other problems associated with nebulizer use alone. In addition, the time taken to deliver the medication with the breath actuated device may vary from three to six times (depending on the ratio of inspiratory to expiratory time) greater than the time taken with the conventional nebulizer to deliver the same dose of medication. Other examples of aerosol inhalation devices can be found in U.S. Pat. No. 4,210,155, in which there is a fixed volume mist accumulation chamber for use in combination with a nebulizer and a TEE connection.

Problems with prior art devices include that the devices significantly waste medication, they provide a non-uniform concentration of delivered medication, they provide a non-uniform concentration of delivered gas, they are expensive, and they are difficult to use. Many of these devices are commercially available in which the nebulizer is directly attached to the TEE connector without any mixing chamber. All of the aforementioned devices can be used with either an MDI or a nebulizer but not both, and hence, face the difficulty associated with either system alone. Other devices have tried to overcome the above problems by incorporating a mixing chamber in the device with adaptability to be used with an MDI or standard nebulizer. U.S. patent application publication No. 2002/0121275 disclosed a device having the above characteristics. However, this device is plagued with problems that are typical to those type of devices. As with other conventional devices, the disclosed device, like the other ones, fails to incorporate some of the key features necessary for enhanced aerosol delivery.

In general, each of the prior art devices suffers from the following deficiencies: (1) the entrained airflow in the device interferes with the MDI plume as well as the plume generated by a nebulizer resulting in increased impaction losses of aerosol generated by either an MDI or nebulizer; (2) the device does not have the ability to deliver a desired precise fraction of inspired oxygen to a hypoxic patient and simultaneously deliver aerosol medication with either a metered dose inhaler (MDI) or a nebulizer; (3) the device can not deliver a gas with a desired density to improve aerosol delivery and a desired fraction of inspired oxygen to a hypoxemic patient; (4) the device does not have the ability to deliver different density gases with a desired fraction of inspired oxygen simultaneously while retaining the ability to deliver aerosol medication at the same time with either an MDI or a nebulizer; (5) the device does not have the ability to deliver a mixture of multiple gases to a patient and simultaneously maintain a desired fraction of inspired oxygen; (6) the device does not serve as a facemask for delivering varying concentrations of inspired oxygen from room air to 100% but serves solely as an aerosol delivery device; (7) the device does not have a reservoir chamber—either as a bag or as a large volume tubing to store nebulized medication that is otherwise wasted during exhalation (The holding chamber of this type of device varies from 90 cc to 140 cc and is not enough to serve as a reservoir for the volume of nebulized medication generated during exhalation which is, therefore, wasted); (8) there is no mechanism in the device to prevent entrainment of room air which forms the bulk of volume during inhalation (the fraction of inspired oxygen and the density of the gas mixture inhaled by the patient may vary with every breath with the device depending on the volume of entrained room air which may vary with each breath); (9) the device does not have any valve system to prevent exhaled carbon dioxide from entering the holding chamber—rebreathing of carbon dioxide from the holding chamber on subsequent inhalation can be extremely detrimental to a patient and extremely dangerous under certain clinical conditions; (10) the device does not have the capability of delivering medication with an MDI and a nebulizer simultaneously; and (11) the device has a fixed volume-holding chamber, which makes the device extremely large and cumbersome to deliver medication.

What is needed in the art and has heretofore not been available is a system that overcomes the above deficiencies and incorporates functionality to make the device a compact, user friendly, economical, and multipurpose aerosol device for both acute and chronic use with either an MDI or a nebulizer or with both devices simultaneously as warranted by the patient's clinical circumstances.

SUMMARY

According to one aspect of the present invention, an aerosol inhalation system including an accessory is defined by a first conduit member for delivering medication in the form of aerosol particles to a patient, as well as a first holding chamber for holding the aerosol particles prior to delivery to the first conduit member. The accessory includes a valve mechanism associated with the first conduit member and including a first valve assembly and a second valve assembly. The first valve assembly is positionable between an open position and a closed position where the fluid is prevented from flowing between the first holding chamber and the first conduit member as when the patient exhales. The first valve assembly assumes the open position as the patient inhales. The second valve assembly is positionable between an open position where the first conduit member is vented to atmosphere as when the patient exhales and a closed position when the patient inhales and the first valve assembly opens.

The aerosol inhalation system includes at least one device in fluid communication with the first holding chamber for producing the aerosol particles. For example, the device can be either an MDI, a nebulizer or both devices can be used simultaneously. According to one exemplary embodiment of the present invention, the aerosol inhalation system is a closed system and is therefore capable of delivering a fixed concentration of the medication and a fixed concentration of delivery gas to the patient thereby overcoming the above deficiencies that are associated with the prior art devices.

In one embodiment, the first holding chamber has a variable interior volume as by a having a variable length such that when the length of the first holding chamber is at a minimum, the interior volume thereof is at a minimum and when the length of the first holding chamber is at a maximum, the interior volume thereof is at a maximum. The first holding chamber can be defined by a body that is collapsible and expandable in length so as to vary the interior volume and therefore, can be in the form of a bellows structure in one embodiment or can be in the form of two single open-ended tubular structures one nested inside the other.

Optionally, the system can include a second holding chamber in fluid communication with the first holding chamber and including a first port for attachment to at least one device. The second holding chamber can have a variable interior volume and therefore, a number of different interior volume settings can be achieved by simply altering one or more of the interior volumes of either the first holding chamber, the second holding chamber or both.

According to another aspect of the present invention, an accessory for an aerosol inhalation system includes a main conduit body having an open first and an opposing open second end; a first port formed as part of the main conduit body; a second port formed as part of the main conduit body; and a first holding chamber operably coupled to second end of the main conduit body and in selective fluid communication with the first end of the main conduit body. The accessory also includes a valve mechanism associated with the main conduit body, as well as a first valve assembly and a second valve assembly. The first valve assembly is positionable between an open position and a closed position where the fluid is prevented from flowing between the first holding chamber and the first port when the patient exhales. The first valve assembly assumes the open position as the patient inhales.

The second valve assembly is disposed in the first port and is positionable between an open position where a portion of main conduit body is vented to atmosphere, when the patient exhales, and a closed position when the patient inhales and the first valve assembly opens.

The first holding chamber has a variable volume and includes a main connector port to permit attachment of at least one device for generating and delivering the aerosol particles to the first holding chamber. This variable volume permits the accessory to be tailor fit for the specific type of patient and in particular permits the accessory to be easily modified on site either use with a person ranging from an infant, a young child, a teen, or an adult. The first holding chamber has an air vent that opens when the patient inhales and closes when the patient exhales to assist in flow of the aerosol particles from the first holding chamber into the main conduit body.

Further aspects and features of the exemplary aerosol inhalation system disclosed herein can be appreciated from the appended Figures and accompanying written description.

BRIEF DESCRIPTION OF THE DRAWING FIGURES

The foregoing and other features of the present invention will be more readily apparent from the following detailed description and drawings of the illustrative embodiments of the invention wherein like reference numbers refer to similar elements and in which.

DETAILED DESCRIPTION OF PREFERRED EMBODIMENTS

Figure 1:
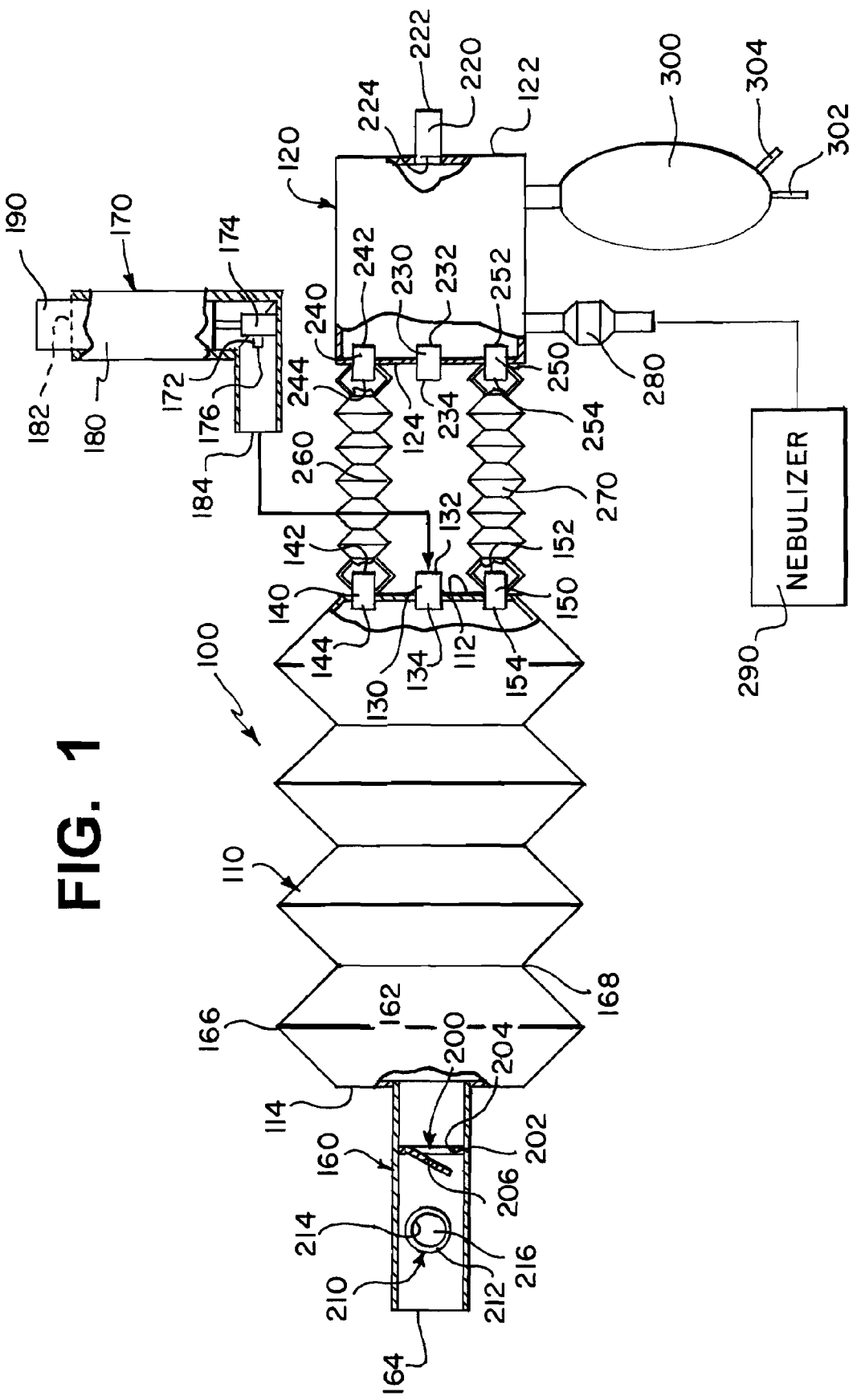
FIG. 1 is a side elevation view of an aerosol inhalation system according to a first embodiment.

Now turning to FIG. 1 in which an aerosol delivery system 100 according to one embodiment is illustrated. The system 100 is constructed and adapted for use with a metered dose inhaler (MDI) or a nebulizer or both.

As previously mentioned, one of the disadvantages of prior nebulizer systems is that the nebulizer is not able to deliver a fixed concentration of medication to the patient since the nebulizer system includes a vented outlet conduit or tube that connects to a mask or the like to permit the suspended medication to be delivered into the patient's body. More particularly, this outlet conduit simply contains a vent opening or the like which permits atmospheric air to flow into the outlet conduit and mix with the nebulized medication that is delivered into the outlet conduit from a holding chamber or the like. It will be appreciated that this results in a mixing of the medication with atmospheric air and this results in the concentration of the medication being diluted due to the presence of air. This is not desirable since it results in medication being delivered at less than a desired concentration as a result of the dilution of the medication by the air.

According to one embodiment, the system 100 includes two defined chambers or compartments, namely a first chamber (holding chamber) 110 and a second chamber (holding chamber) 120 when the system 100 is constructed to function as an MDI delivering device and a nebulizer accessory. The first chamber 110 can alternatively be discussed as being a metered dose inhaler (MDI) chamber, while the second chamber 120 can alternatively be discussed as being a nebulizer chamber. The first chamber 110 has an inlet end 112 as well as an opposing outlet end 114 and similarly, the nebulizer chamber 120 has an inlet end 122 and an opposing outlet end 124. The inlet end 112 is operatively coupled to a plurality of conduit members or connectors and in particular, the inlet end 112 is operatively coupled to a first conduit member (first connector) 130, a second conduit member (second connector) 140 and a third conduit member (third connector) 150. Preferably, each of the conduit members 130, 140, 150 is a hollow tube-like structure that is constructed to carry a fluid from one end to the other end. Relative to the surface defining the inlet end 112 of the chamber 110, the first conduit member 130 is centrally located and therefore can be defined as a central conduit, while the second conduit member 140 is located approximately at a three o'clock position and the third conduit member 150 is located approximately at a nine o'clock position. Due to their positions relative to the centrally located first conduit member 120, the second and third conduit members 130, 140 can be thought of as being peripheral conduit members.

The first conduit member 130 includes an inlet end 132 and an opposing outlet end 134, with the outlet end 134 being in fluid communication with the interior of the first chamber 110. Similarly, the second conduit member 140 includes an inlet end 142 and an opposing outlet end 144, with the outlet end 144 being in fluid communication with the interior of the first chamber 110. Likewise, the third conduit member 150 includes an inlet end 152 and an opposing outlet end 154, with the outlet end 154 being in fluid communication with the interior of the first chamber 110. The operation of the first, second and third conduit members 130, 140, 150 is described in greater detail below.

The first chamber 110 is also operatively coupled to a fourth conduit member 160 that is disposed at the outlet end 114 of the first chamber 110. Similar to the other conduit members, the fourth conduit member 160 has an inlet end 162 and an opposite outlet end 164, with the inlet end 162 being in fluid communication with the interior of the first chamber 110.

According to the present invention, the first chamber 110 is preferably a holding chamber that has an adjustable interior volume and therefore, the volume of the first chamber 110 can be advantageously varied depending upon a number of different parameters, such as the type of patient and more specifically, the weight of the patient. There is a direct correlation between the weight of the patient, and lung capacity, and the volume of the holding chamber 110 in that the greater the weight of the patient, the greater the required volume of the holding chamber 110. In accordance with one aspect of the invention, the volume of the first chamber 110 can be chosen between a number of different selected volumes so as to cater and customize the system 100 for the specific patient. The different settings can be marked on the first chamber 110 or they can be otherwise conveyed to the physician who then merely manipulates the body forming the first chamber 110 so that the volume of the first chamber 110 is within the desired range.

For example, the settings corresponding to the volume of the first chamber 110 can be (1) infant; (2) young child; (3) pre-teen child; (4) teenager; (5) young adult; (6) adult; and (7) elderly. Similarly, the settings corresponding to the volume of the first chamber 110 can be directly correlated to a mass size, such as (1) less than 20 pounds; (2) less than 60 pounds; (3) less than 100 pounds; (4) less than 150 pounds; (5) less than 200 pounds, etc. After determining what the proper setting should be, the physician can then manipulate the first chamber structure to cause the volume within the first chamber 110 to be set at the desired value. In each of the embodiments, the structure defining the first chamber 110 can be manually manipulated resulting in the interior volume of the first holding chamber either being increased or decreased. For example and according to one embodiment, the first chamber 110 can be formed by a first part and a second part that is at least partially received in the interior of the first part and slidingly engages the first part such that when it is desired for the interior volume of the first chamber 110 to be changed, the user simple moves the second part relative to the first part resulting in the interior volume either increasing or decreasing. Accordingly, a pair of slide single open-ended tubular structures respect to one another can be mated together such that they can slide with respect to one another. The structures can contain markings, settings, or graduations so that it is easy for the user to simple adjust one of the parts with respect to the other part until it is in registration with some type of guide line that represents or indicates the volume of the interior of the first chamber 110. In order to provide a sealed first chamber 110, the first and second parts preferably contain some type of seal element that ensures an air-tight seal therebetween. For example, one or both of the first and second parts can contain an O-ring or the like that sealingly engages a surface of the other part while still permitting sliding movement between the two parts.

It will be appreciated that the first and second parts can also be fitted with a locking type mechanism so as to permit the position of the first part relative to the second part to be locked in place. For example, the first part can be at least partially received in the second part such that the first part at least partially surrounds the second part, with the first part having a number of axially aligned opening formed therein. Each opening corresponds to a different interior volume setting. The second part can include a biased projection that protrudes out from the exterior surface thereof and in one particular embodiment, the biased projection is a spring biased push button that can be depressed upon application of force and will return to its original biased position when the applied force is removed. When the second part is received in the first part, the biased projection is in a biased condition and is at least partially depressed and exerting a force against an inner surface of the first part until the projection comes into registration with one of the openings at which time, the biased nature of the projection causes the projection to fire into the opening, thereby locking the position of the first part relative to the second part. To freely adjust the interior volume of the first chamber 110, the projection can simply be depressed until it clears the first part and then the second part can be moved relative to the first part in a direction toward the next desired opening at which time the projection is received in the opening, thereby locking the two parts in a different setting with a different interior volume.

Figure 2:
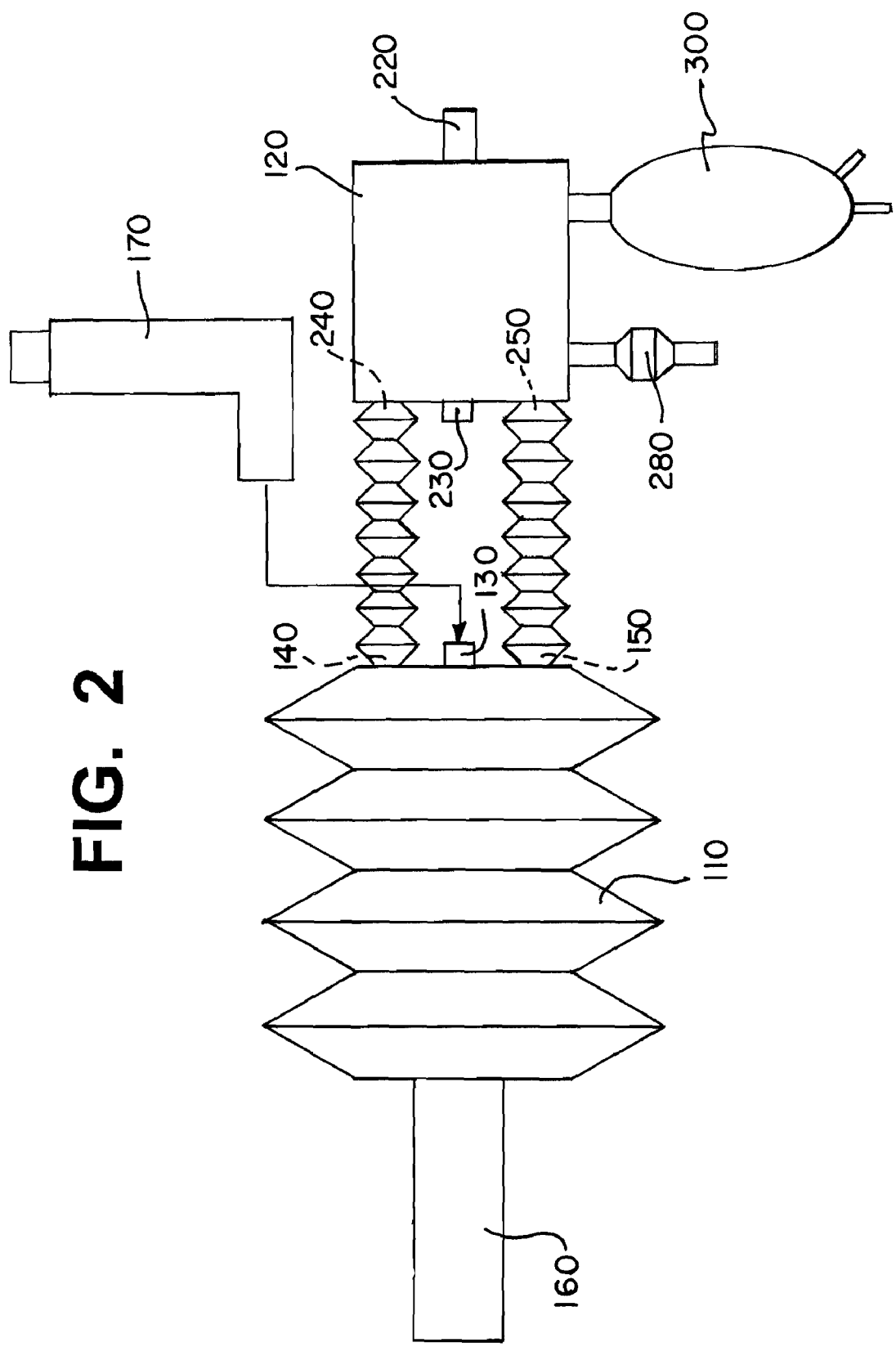
FIG. 2 is a side elevation view of the aerosol inhalation system of FIG. 1 with a first holding chamber in a collapsed state.

The first chamber 110 can be made of any number of different materials, including plastic, paper or even a metal so long as the interior volume thereof can be varied. According to one embodiment, the first chamber 110 can have a cylindrical shape with smooth edges or it can by cylindrical in shape with a series of ridges 166 and recesses or valleys 168 that alternate with one another so as to represent a bellows or accordion type structure. Alternatively, the first chamber 110 can be supported with a metal or plastic coil that includes multiple ring structures so as to support the material that defines the body of the first chamber 110. The distances between any two adjacent ridges 166 can be equal as in the case of a uniform structure or the distances can be different. In another embodiment, the first chamber 110 can be formed of a stiff corrugated plastic that preferably does not require any additional support to maintain the shape of the first chamber 110. FIG. 1 shows the first chamber 110 in an expanded state (e.g., fully expanded state), while FIG. 2 shows the first chamber 110 in a fully collapsed state. It will be appreciated that the first chamber 110 can be constructed in any number of different ways so long as the first chamber 110 has a variable interior volume.

A metered dose inhaler 170 is provided and can be any number of commercially available inhalers that are configured to deliver a metered dose of medication, etc. The inhaler 170 has a boot structure 180 that has an inlet end 182 and an opposing outlet end 184. The illustrated boot structure 180 is generally an L-shaped hollow structure with the outlet end 184 being formed in a boot section that is perpendicular to another section that terminates with the inlet end 182. A canister 190 is introduced into the boot structure 180 through the inlet end 182 of the boot 180 and a nozzle 172 of the inhaler 170 is attached to an actuator 174. The actuator 174 has an opening or slot 176 formed therein and preferably, the actuator 174 is positioned so that the opening 176 faces and is in fluid communication with the first conduit member 130. Upon actuation of the MDI canister 190, the medication aerosol particles are generated through the opening 176 of the actuator 174 and enter into the MDI chamber 110 through the outlet end 134 of the first conduit member 130.

The fourth conduit member 160 that is associated with the first chamber 110 preferably has at least one valve assembly for controlling the fluid flow into and out of the first chamber 110 as the patient inhales and exhales. In the illustrated embodiment, the fourth conduit member 160 has two valve assemblies, namely, a first valve assembly 200 and a second valve assembly 210, that are located between the ends 162, 164. The first valve assembly 200 can be thought of as an inhalation valve assembly and a second valve assembly 210 can be thought of as an exhalation valve assembly. The inhalation valve assembly 200 can be a flap valve assembly that includes a circular flap valve seat 202 that has a circular opening 204 and a complementary flap valve 206 that seats against the seat 202 to close opening 204 when the valve assembly 200 is closed. Similarly, the exhalation valve assembly 210 can be a flap valve assembly that includes a circular flap valve seat 212 that has a circular opening 214 and a complementary flap valve 216 that seats against the seat 212 to close the opening 214 when the valve assembly 210 is closed.

On inhalation, the inhalation flap valve 206 moves away from the valve seat 202 so that the aerosol particles can move from the first chamber 110 to the patient (e.g., mouth and lungs of the patient) through the opening 204 in the seat 302 and then ultimately through the outlet end 134 of the fourth conduit member 130. Conversely, on exhalation, the flap valve 206 moves toward the valve seat 202 and closes the opening 204 to prevent any flow of gas exhaled by the patient from entering into the first chamber 110, thereby avoiding re-breathing of carbon dioxide on the next inhalation. The flap valve seat 202 prevents any protrusion of the flap valve 206 through the opening 204.

The flap valve 216 of the exhalation flap valve assembly 210 presses against the flap valve seat 212 on inhalation and completely occludes the opening 214 to prevent any room air entrainment (i.e., not allowing the air from the atmosphere to enter into the fourth conduit member 130 on inhalation). On exhalation, the flap valve 216 moves away from the flap valve seat 212 for the air exhaled by the patient to escape into the atmosphere from the fourth conduit member 130 through the opening 214.

The second chamber 120 can serve as a nebulizer chamber or a second holding or retaining chamber when the first chamber 110 functions as an MDI chamber 110, thereby permitting the system 100 to support either the use of an MDI or a nebulizer or both.

The second chamber 120 has an associated fifth conduit member 220 that has an inlet end 222 and an opposing outlet end 224. In one embodiment, the fifth conduit member 220 is in the form of a hollow cylindrical inlet tube, with its inlet end 222 be adapted to be attached to a single gas source or multiple gas sources to obtain a mixture of gases with a desired density, oxygen concentration, viscosity, and humidity to improve the delivery of aerosol particles as well as to deliver a fixed concentration of oxygen to a hypoxemic patient. The second chamber 120 also can have associated therewith a sixth conduit member 230 that has an inlet end 232 and an opposing outlet end 234. The sixth conduit member 230 can be in the form of a hollow cylindrical outlet tube, with its outlet end 234 remaining plugged with a plug (e.g., a cap) when the device 100 is in use with the metered dose inhaler 170.

The illustrated second chamber 120 also has additional conduit members that are associated therewith and more specifically, the second chamber 120 includes a seventh conduit chamber 240 and an eighth conduit member 250. Each of the conduit members 240, 250 can be in the form of a hollow cylindrical tube that are peripherally orientated relative to the sixth conduit member 230 and more specifically, the conduit member 240, 250 are located at approximately a 3 o'clock position and a 9 o'clock position, respectively, relative to the sixth conduit member 230.

Figure 3:
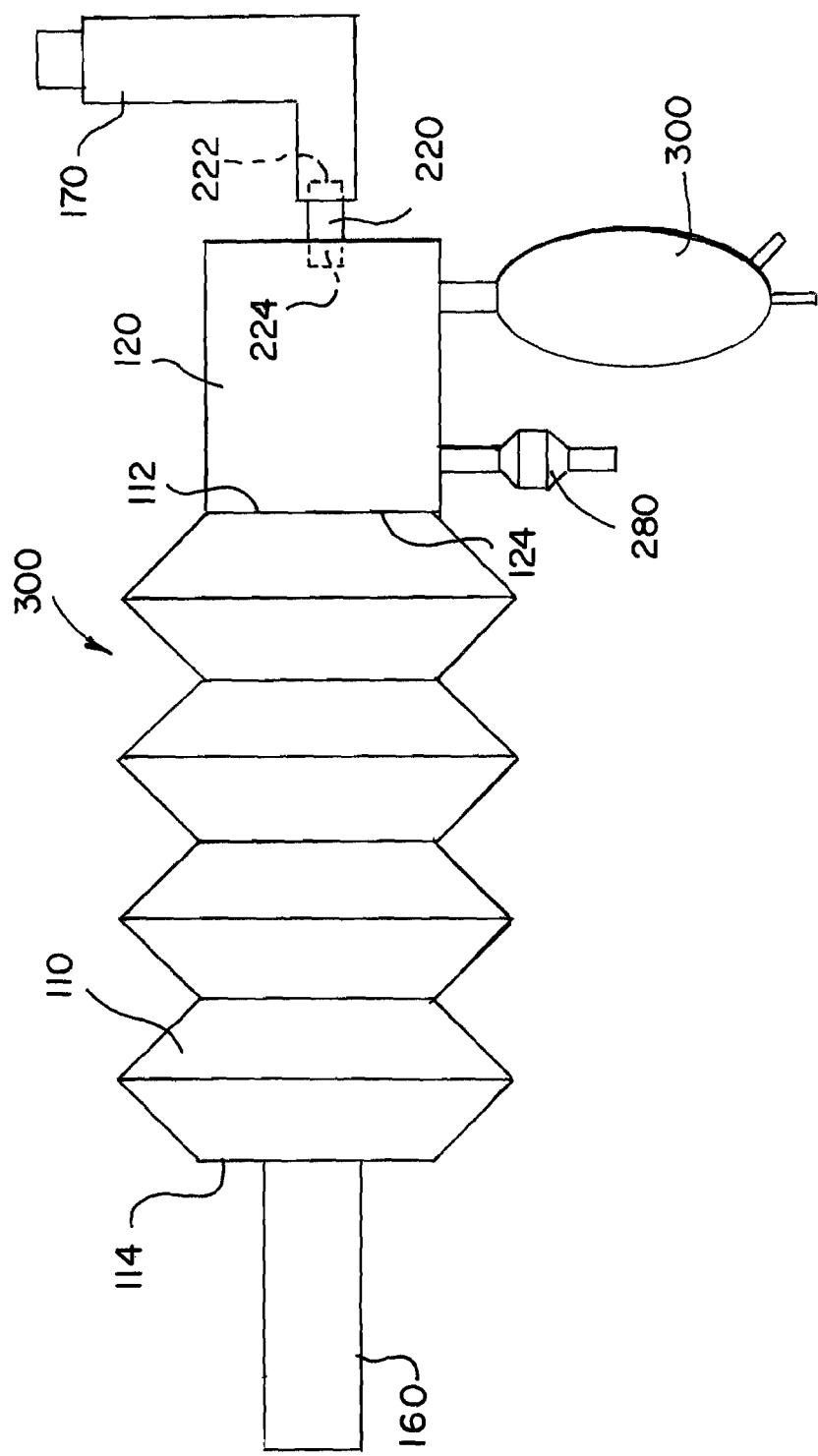
FIG. 3 is a side elevation view of an aerosol inhalation system according to a second embodiment.
Figure 4:
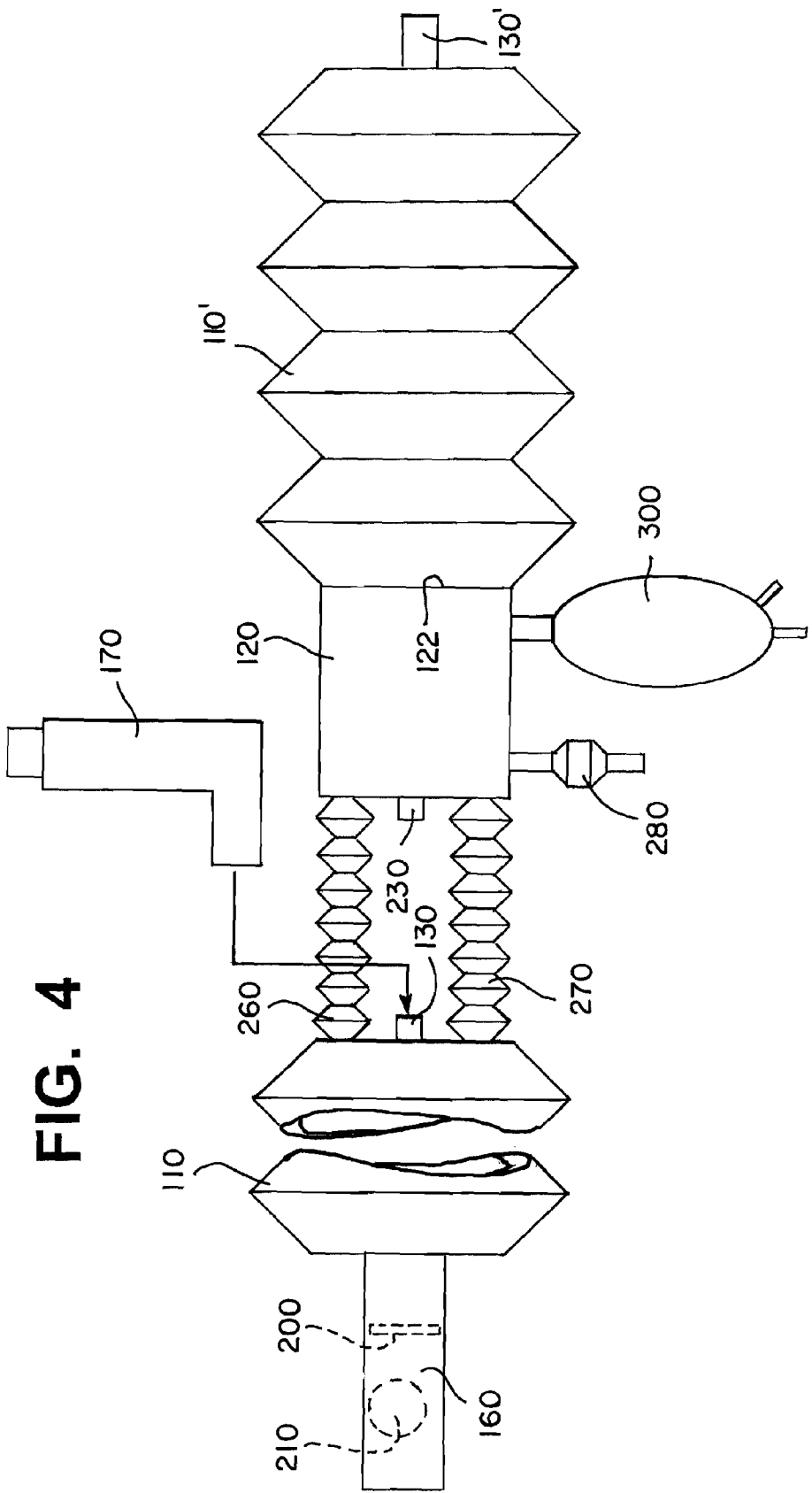
FIG. 4 is a side elevation view of an aerosol inhalation system according to a third embodiment with first and second holding chambers in fully expanded states.
Figure 5:
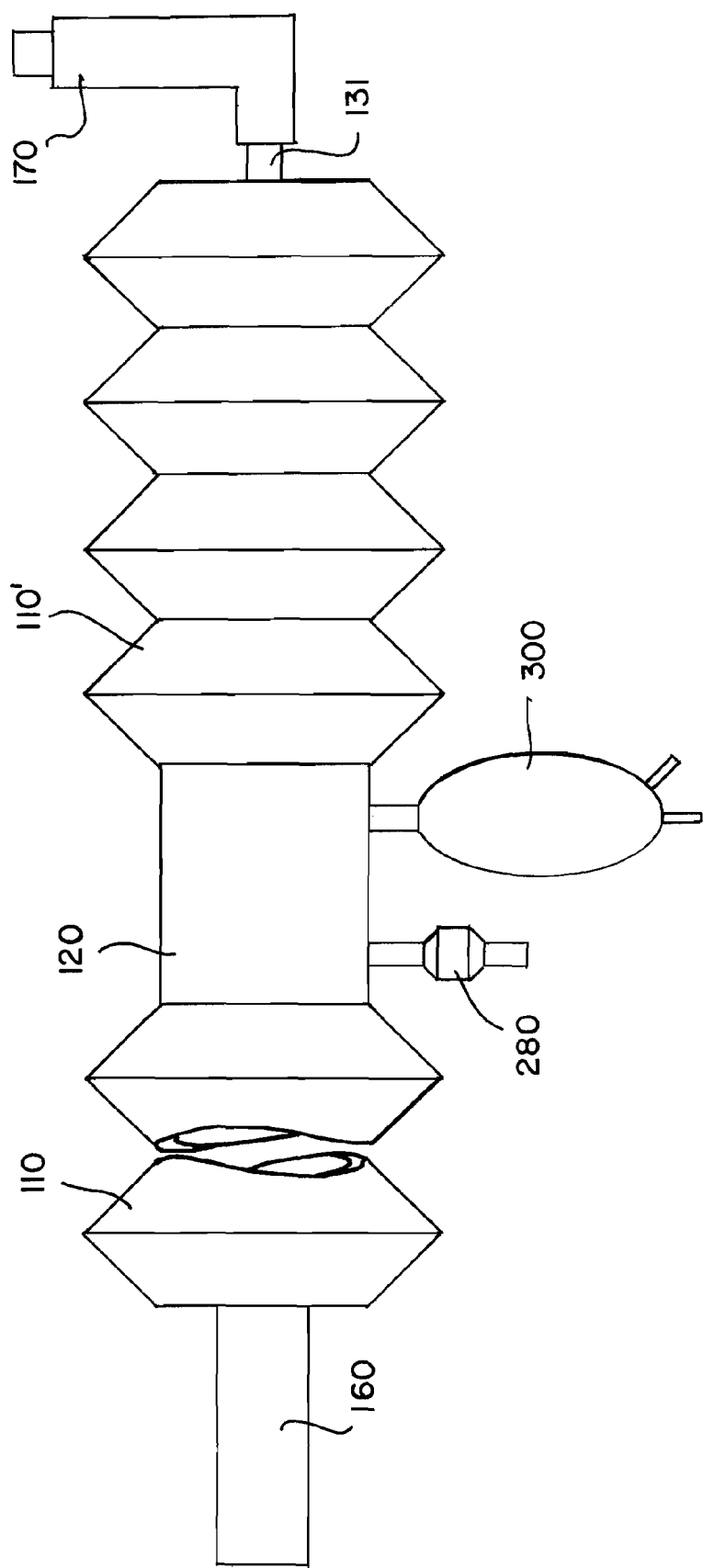
FIG. 5 is a side elevation view of an aerosol inhalation system according to a fourth embodiment with first and second holding chambers in fully expanded states.
Figure 6:
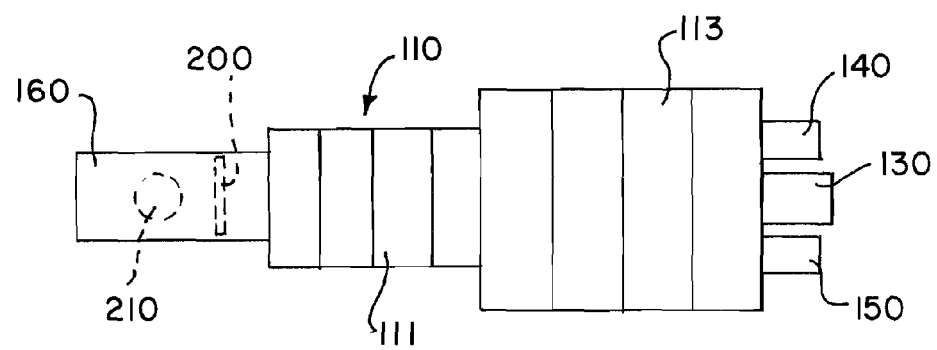
FIG. 6 is a side elevation view of a collapsible/expandable holding chamber according to an alternative embodiment.

The seventh conduit member 240 has an inlet end 242 and an opposing outlet end 244 and similarly, the eighth conduit member 250 has an inlet end 252 and an opposing outlet end 254. The inlet end 142 of the second conduit member 140 at the inlet end 112 of the MDI chamber 110 is fluidly and preferably sealingly connected to the outlet end 244 of the seventh conduit member 240 by means of a first collapsible/expandable fluid connector 260. The first collapsible/expandable fluid connector 260 can be in the form of a collapsible/expandable stiff corrugated plastic tubing or other similar structure that has a variable length due to its expandable/collapsible nature. Similarly, the inlet end 152 of the third conduit member 150 at the inlet end 112 of the chamber 110 is fluidly and preferably sealingly connected to the outlet end 254 of the eighth conduit member 250 by means of second collapsible/expandable fluid connector 270. The second collapsible/expandable fluid connector 270 can be in the form of a collapsible/expandable stiff corrugated plastic tubing. In FIGS. 1 and 3, the collapsible/expandable corrugated plastic tubes 260, 270 are demonstrated in a fully expanded state in order to accommodate the boot 180 between the first chamber 110 and the second chamber 120.

The second chamber 120 has a first inlet port 280 formed as a part thereof for connection with a standard small volume nebulizer 290. As is known, a nebulizer is a device that changes liquid medicine into fine droplets (in aerosol or mist form) that are inhaled through some type of device, such as a mouthpiece or mask, etc. The second chamber 120 also has another inlet in the form of a second inlet port 290 for connection to a reservoir bag 300. The reservoir bag 300 serves to store the aerosol particles generated by the nebulizer 290 during the exhalation phase to be inhaled on the next breath, thereby improving aerosol medication delivery. The reservoir bag 300 can be made of any number of different materials, including plastic, neoprene, paper or even metal. The illustrated reservoir bag 300 has two small inlet ports 302, 304 that are configured and intended to be connected to one or more gas sources to obtain a mixture of gases with a desired density, oxygen concentration, viscosity and humidity to improve the delivery of aerosol particles as well as deliver a fixed concentration of oxygen to a hypoxemic patient.

According to the present invention, the system 100 provides a closed nebulizer arrangement that offers improved performance compared to the prior art nebulizer systems which were not closed, as previously mentioned, but instead were vented to atmosphere at a location just prior to or at the interface where the nebulized medication was delivered to the patient's mask or the like. The atmospheric venting of the prior art designs leads to the dilution of the concentration of the medication being delivered to the patient, which is not desirable, since the physician initially prescribes a concentration of medication that is to be delivered to the patient and preferably, this concentration is to remain unchanged as it is delivered from the nebulizer into the patient's body. As can be seen from FIG. 1 and the accompanying description, the present system 100 does not contain an atmospheric vent that is open during the delivery of the nebulized medication. While there is a pair of valve mechanisms in the fourth conduit member 160 that is associated with the first chamber 110, these valves function so that the nebulized medication that is held within the first and second compartments 110, 120 is delivered to the patient's body as the patient inhales. As previously mentioned, on inhalation, the inhalation flap valve 206 moves away from the valve seat 202 so that the aerosol particles can move from the first chamber 110 to the patient (e.g., mouth and lungs of the patient) through the opening 204 in the seat 302 and then ultimately through the outlet end 134 of the fourth conduit member 130. The flap valve 216 of the exhalation flap valve assembly 210 presses against the flap valve seat 212 on inhalation and completely occludes the opening 214 to prevent any room air entrainment (i.e., not allowing the air from the atmosphere to enter into the fourth conduit member 130 on inhalation). This therefore leads to be a completely closed nebulizer system that ensures delivery of medication having a fixed concentration, unlike the prior art systems.

Figure 7:
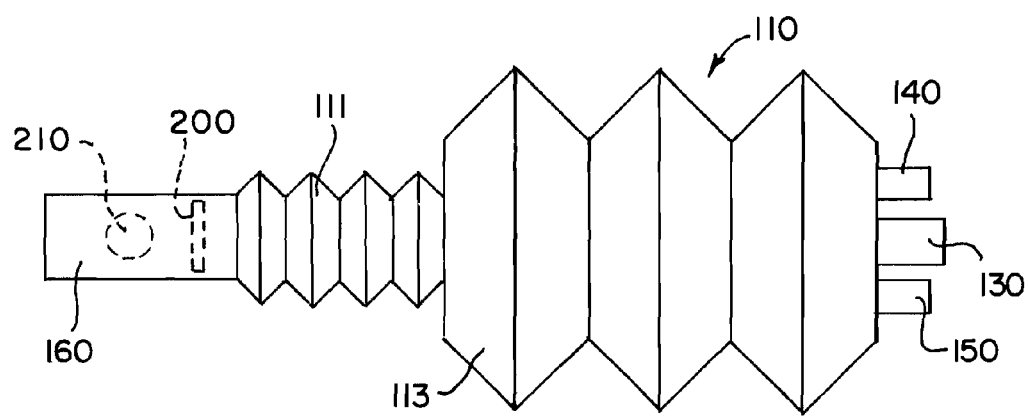
FIG. 7 is a side elevation view of a collapsible/expandable holding chamber according to another alternative embodiment.
Figure 8:
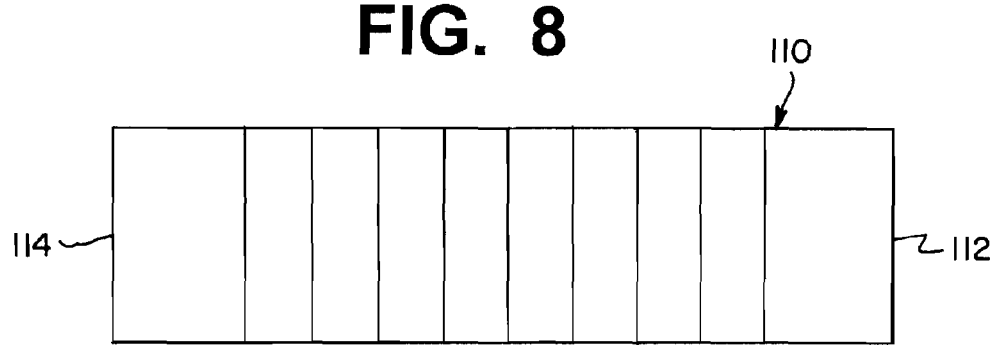
FIG. 8 is a side elevation view of a collapsible/expandable holding chamber according to an alternative embodiment.
Figure 9:
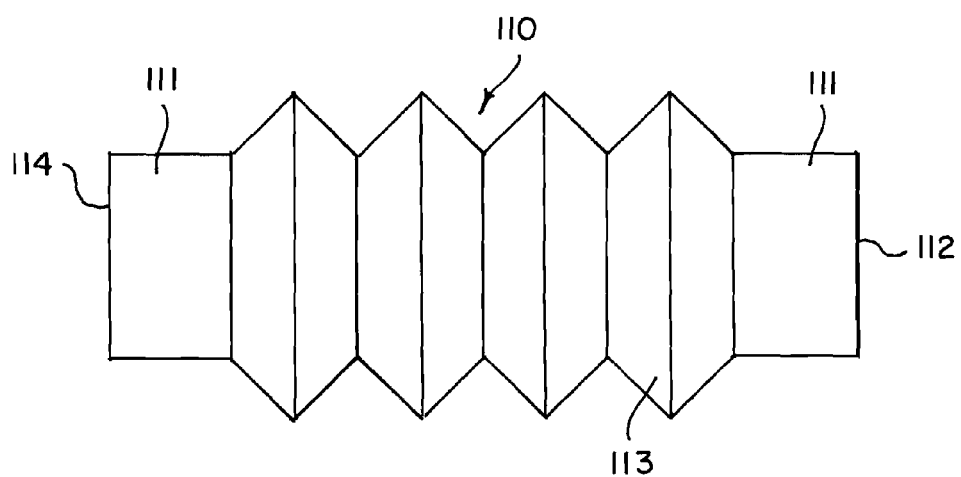
FIG. 9 is a side elevation view of a collapsible/expandable holding chamber according to yet another alternative embodiment.

To alter the holding capacity of the first chamber 110, the distance between two adjacent ridges 166, rings of associated coils, or valleys 168 is reduced by pulling the two adjacent structures together in the case of when the structure forming the first chamber 110 has a bellows type construction. When fully collapsed, the inlet end 162 of the fourth conduit member 160 can engage the outlet end 134 of the first conduit member 130. The first and second collapsible/expandable corrugated plastic tubes 260, 270 can be fully extended or expanded in order to accommodate the MDI boot 180 between the first chamber 110 and the second chamber 120.

It will also be appreciated that in an alternative arrangement between the metered dose inhaler 170 and the rest of the device 100 and unlike the embodiment of FIG. 1, the inlet end 132 of the first conduit member 130 does not have to be attached to the inhaler 170 but instead the inhaler 170 can be a separate component. The inlet end 162 of the fourth conduit member 160 can engage (e.g., be fused or bonded) the outlet end 234 of the sixth conduit member 230, while the inlet ends 142, 152 of the second and third conduit members 140, 150 can engage (e.g., be fused or bonded) to the outlet ends 244, 254 of the seventh conduit chamber 240 and an eighth conduit member 250, respectively, or the second and third conduit members 140, 150 can remain separate from and not bondingly coupled to the seventh and eighth conduit members 240, 250.

In this embodiment, the inhaler (MDI) 170 can be connected to the inlet end 222 of the fifth conduit member 220 associated with the second chamber 120 and upon actuation of the inhaler 170, the aerosol particles generated by the MDI 170 are discharged into the nebulizer chamber 120 and into the first chamber 110 via the sixth, seventh, and eighth conduit members 230, 240, 250. In other words, the aerosol particles are delivered from the second chamber 120 into the first chamber 110 by means of the central connection (sixth conduit member) 230 and the two peripheral connections (seventh and eighth conduit members 240, 250) between the two chambers 110, 120.

FIG. 2 shows the first chamber 110 in a fully collapsed position.

FIG. 3 shows another alternate embodiment of a device 300 that is similar to device 100 of FIG. 1 and therefore like parts are numbered alike. The device 300 is constructed so that it can be used with either a metered dose inhaler (MDI) or a nebulizer or both. In this embodiment, the inlet end 112 of the first chamber 110 and the outlet end 124 of the second chamber 120 are securely coupled to one another. For example, the ends 112, 124 can be bonded or fused to one another along an interface edge therebetween which in this case is a circumferential edge since both chambers 110, 120 are cylindrical in shape. Any number of means for bonding or otherwise securely attaching these two ends 112, 124 to one another can be used. For example, the two can be heat sealed or adhesively bonded to one another or fused to one another. In this figure, the first chamber 110 is shown in the fully expanded state. In this embodiment, the inhaler 170 is directly coupled to the fifth conduit member 220 and more particularly, the inhaler (MDI) 170 is connected to the inlet end 222 of the fifth conduit member 220 associated with the second chamber 120 and upon actuation of the inhaler 170, the aerosol particles generated by the MDI 170 are discharged into the second chamber 120 and into the first chamber 110.

The inlet end 222 of the fifth conduit member 220 can have a boot adapted assembly to accommodate the boot 180 of any commercially available inhaler (MDI) 170. Upon actuation of the inhaler 170, the aerosol particles generated in the inhaler 170 are discharged into the nebulizer chamber 120 and into the MDI chamber 110. In particular, on actuation of the MDI canister 190, the medication aerosol particles are generated through the opening 176 of the actuator 174 and then is delivered through the lower section of the boot 180 and into the inlet end 222 of the fifth conduit member 220.

FIG. 4 shows another alternative embodiment where there are two first chambers 110, 110' instead of just one first chamber 110. In this configuration, the additional first chamber 110' is formed and interfaces with the end 122 of the second chamber 120, thereby resulting in the second chamber 120 being disposed between the two first chambers 110, 110'. This alternative embodiment thus provides two chambers (first chamber 110, 110') that each has a variable interior volume that can be customized in view of patient needs, etc. The MDI 170 can be attached in several different locations as in earlier embodiments and in particular, the MDI 170 can be attached at either the first conduit member 130 which forms an entrance into the first chamber 110 or the MDI 170 can be attached to another conduit member 131 that forms an entrance into the first chamber 110'.

In this embodiment, the apparatus can be configured so that for a certain class of patients, such as children or other smaller weight individuals, one of the first chambers 110, 110' remains in the fully retracted (compact) position, while the other first chamber 110, 110' is at least partially expanded to create a prescribed volume that is suited for this type of patient. For larger patients, such as adults or heavy set children, the other chamber 110, 110' can be at least partially expanded to increase the overall available interior volume of the first chamber 110, 110'.

Once again, the extendable nature of the first and second collapsible/expandable fluid connectors 260, 270 permits the MDI 170 to be disposed between the first chamber 110 and the second chamber 120 or the MDI 170 can be attached to the end of the first chamber 110'. This configuration can also be used with a nebulizer based system since the nebulizer can be attached to the second chamber 120 and the overall holding chamber volume to retain the nebulized medication can be varied by either expanding or contracting the volume of the pair of first chambers 110, 110'.

FIG. 5 shows another embodiment similar to the embodiment in FIG. 4 except that the MDI 170 is attached to the conduit 131 at the end of the first chamber 110' instead of being placed between the first chamber 110 and the second chamber 120. As a result, the conduits 130, 140, 150 are eliminated and the interface between the first chamber 110 and the second chamber 120 is made cleaner.

As shown in FIGS. 6-9, it will also be understood that in each of the present embodiments, the first chamber 110, 110' can be constructed in any number of different ways to provide a chamber having a variable interior volume as by having a variable length chamber or by otherwise altering the characteristics of the chamber. For example, the chamber 110, 110' may have a uniform diameter throughout its length or alternatively, the diameter of the chamber 110 may be uniform for a predetermined length of the chamber and then the diameter can change to a different diameter for the remaining length of the chamber as shown in FIGS. 6-7. For example, the chamber can have two distinct sections 111, 113 with each section having a different diameter and in particular, the first section 111 can have a fixed diameter and the second section 113 can have also have a fixed diameter that is different from the fixed diameter in the first section 111 or the second section 113 can have a progressively varying diameter. The first chamber 110, 110' can be formed of any different number of materials and when certain light-weight materials (e.g., paper) are used, a support structure, such as a metal or plastic coil with multiple rings, (see FIG. 8) can be used to maintain the form of the chamber 110, 110' in either the collapsible or the expandable state. However, these support structures may not be needed if the material that forms the first chamber is robust enough as is the case when the material is a stiff material, such as a stiff corrugated plastic material that retains the ability to be collapsible/expandable and at the same time does not require any additional support to maintain the integrity of the chamber. When the chamber includes sections having two different diameters, the support structure (coils) will likewise have different diameters in the two sections, and it can be manipulated by the physician so that each of the different sections of the chamber can either be placed into an expanded or collapsed state. Thus, with respect to the embodiment in FIG. 7, the larger second section 113 of the first chamber 110 can be compressed so that is it fully collapsed, while the first section 111 is fully opened and extended. This arrangement can be used for smaller patients, such as children; and when the apparatus is used with larger sized patients, the second section 113 can be opened to a partial or fully extended state as shown in FIG. 7. In FIG. 9, the larger diameter second section 113 is actually disposed between two uniform smaller diameter first sections 111.

The collapsible/expandable members of the present invention can be formed of any number of different materials, such as plastic, paper or metal and the conduits can have a uniform diameter or they can have two or more sections of different diameters. Depending upon the material used to construct the conduits, reinforcing structures, such as coils or the like, may or may not have to be used similar to those embodiments described earlier.

Figure 14:
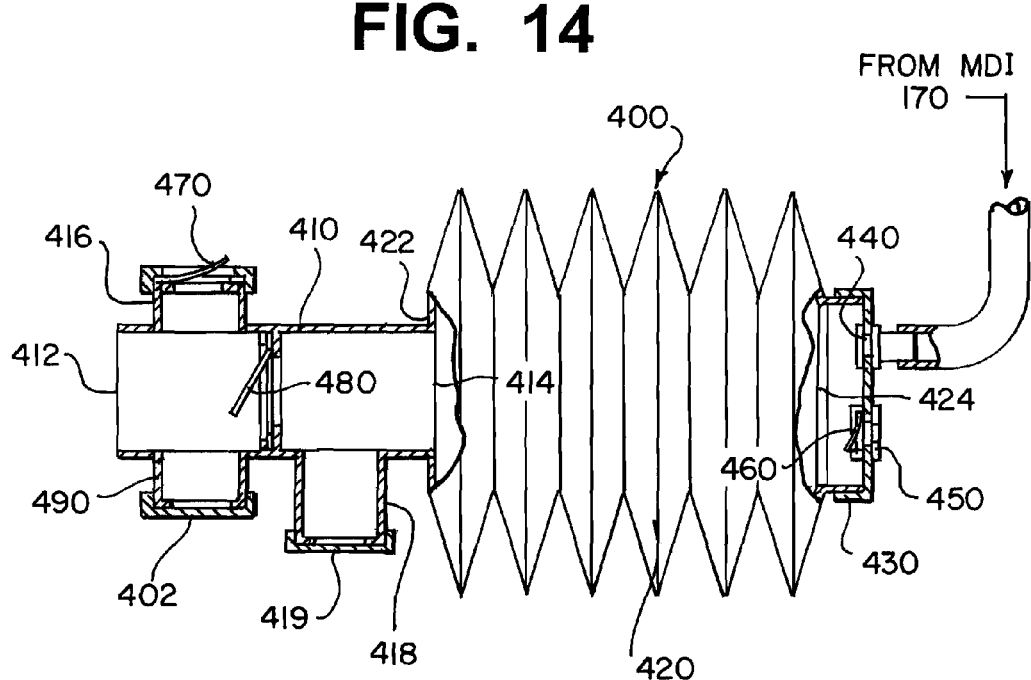
FIG. 14 is a cross-sectional view of the aerosol inhalation accessory of FIG. 13.
Figure 13:
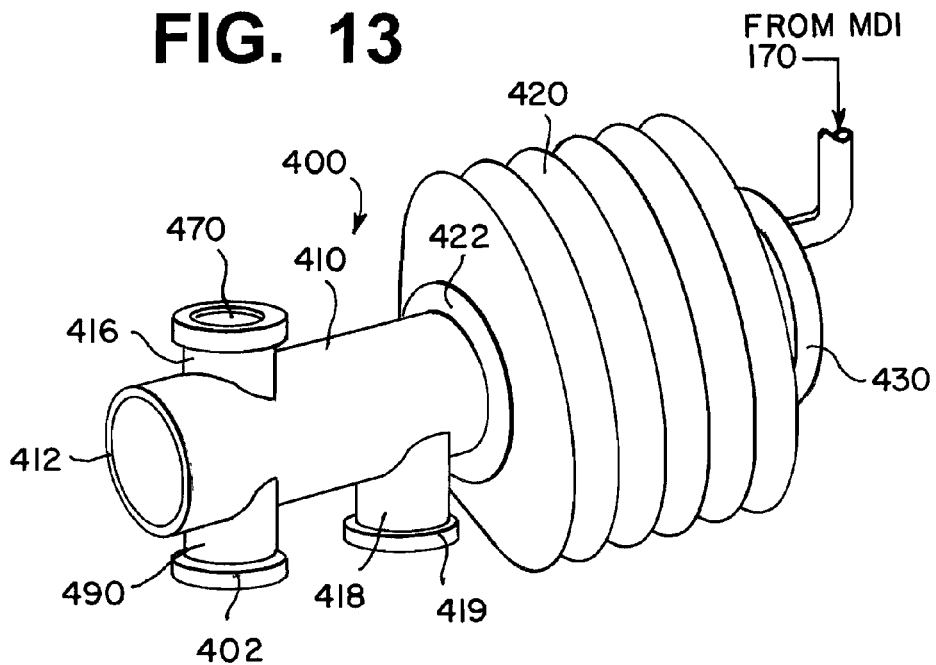
FIG. 13 is a side perspective view of an aerosol inhalation accessory according to a sixth embodiment.

Now referring to FIGS. 13-14 which illustrate an apparatus 400 according to another embodiment of the present invention. The apparatus 400 includes a main delivery conduit 410 that controllably delivers medication to the patient and is adapted to be used with a mask or the like or some other type of structure that is fitted to the patient to deliver the medication to the patient's mouth or into the breathing passageway, etc. The main deliver conduit 410 is formed of a body that has a first end 412 and an opposing second end 414. The conduit 410 is generally a hollow body and includes a first port 416 and a second port 418. In the illustrated embodiment, the first and second ports 416, 418 are formed such that they face in opposite directions. For example, the first port 416 is closer to the first end 412 and therefore closer to the patient, and faces generally upward, while the second port 418 is closer to the second end 414 and faces downward. Each of the ports 416, 418 is in the form of an opening or passageway that is formed in the body 410 and provides an entrance into the interior of the main conduit body 410.

The main delivery conduit 410 is operably and fluidly connected to a holding chamber 420. As with the previous embodiments, the holding chamber 420 can have a fixed interior volume or it can have a variable interior volume. In the illustrated embodiment, the holding chamber 420 has a variable interior volume as a result of the holding chamber being collapsible or expandable as for example, by altering the length of the holding chamber 420. In other words, the holding chamber 420 can be manipulated so that the interior volume thereof is either increased or decreased. In the illustrated embodiment, the holding chamber 420 has a bellows type or accordion type structure such that the walls defining the holding chamber 420 can be collapsed, thereby decreasing the volume of the holding chamber 420. Conversely, the walls of the holding chamber 420 can be expanded so as to increase the volume of the holding chamber 420. It will also be understood that the other structures previously disclosed herein can be used to construct a holding chamber that has a variable interior volume. For example, two tubes that are open ended at one end can be mated with one another in a sliding manner so as to provide a chamber of varying interior volume.

The holding chamber 420 has a first end 422 that mates with the second end 414 of the main conduit body 410 and an opposing second end 424. It will be appreciated that the main conduit body 410 and the holding chamber 420 can be a single integral structure or the holding chamber 420 can be operably and sealingly connected to the main conduit body 410. For example, an outer peripheral edge of the wall of the holding chamber 420 can be sealingly attached to the second end 414 of the main conduit body 410.

The second end 424 of the holding chamber 420 can have an integral end connector 430 or the second end 424 can be operably and sealingly attached to the second end 424 of the holding chamber 420. The end connector 430 closes off the second end 424 of the holding chamber 420. The end connector 430 includes a first port 440 that is adapted to be attached to an MDI, such as MDI 170 of FIG. 1, thereby, permitting particles discharged from the MDI 170 into the interior of the holding chamber 420. The end connector 430 also includes an atmospheric vent port 450 which is merely an opening through the end connector 430 to provide a fluid entrance into the interior of the holding chamber 420 from outside. A valve 460 for the atmospheric vent port 450 is provided on the interior face of the end connector 430 proximate the atmospheric vent port 450 and is positionable between an open position, where fluid (atmospheric air) from outside can enter the interior of the holding chamber 420, and a closed position where the valve 460 seats against the atmospheric vent port 450. The valve 460 can be in the form of a flap valve that is operably attached to the interior face of the end connector 430.

In one embodiment, the second port 418 is intended to be a nebulizer port and is therefore constructed to attach to a nebulizer, a gas source, etc. When the apparatus is intended to be used only as a means for delivering medication from an MDI, the second port 418 can simply be closed off by a cap 419 or the like. When it is desired for a nebulizer or gas source to be fluidly connected to the main conduit body 410, the cap 419 is simply removed and the nebulizer or gas source is simply sealingly attached to the second port 419 as by threadingly mating the two together.

The first port 416 has a first valve 470 disposed therein which moves between an open position and a closed position depending upon whether the patient is inhaling or exhaling. In particular, the first valve 470 is similar to the valve 210 illustrated in FIG. 1. Within the hollow body of the main conduit 410, there is a second valve 480 that occludes the passageway (conduit) formed in the body when it is a fully closed position. The second valve 480 is similar to the valve 200 of FIG. 1 and is located in the conduit between the first port 416 and the second port 418 and moves between an open position and a closed position. In one embodiment, the second valve 480 is an inhalation valve assembly and can be formed of a flap valve that interfaces with and seats against a shaped flap valve seat when the second valve 480 is in the closed position. When the second valve 480 is closed, fluid is prevented from flowing from the second end 414 to the first end 412 and in particular, fluid is prevented from flowing between the first and second ports 416, 418.

Similarly, the first valve 470 is similar to the valve 210 in FIG. 1 and therefore functions as an exhalation valve and can be formed of flap valve that interfaces with and seats against a shaped flap valve seat when the first valve 470 is in the closed position. The first valve 470 thus moves between an open position and a closed position.

When the apparatus is intended for use with only an MDI, the second port 418 is closed with the cap 419 and on inhalation, the second valve 480 moves away from its respective valve seat and permits flow of fluid toward the first end 412 of the main conduit 410, thereby permitting aerosol particles to move from the MDI 170 into the holding chamber 420, into the second end of main conduit body 410 and then through the main conduit body 410 to the patient. On inhalation, the first valve 470 (exhalation valve) remains in the closed position, thereby preventing the flow of air into the main conduit body 410. In other words, on inhalation, the flap valve 470 completely occludes the opening formed at the first port 416 to prevent room air entrainment, i.e., not allowing the air from the atmosphere to enter the main conduit 410.

Unlike the earlier embodiments, including the embodiment of FIG. 1, this embodiment shown in FIGS. 13-14 is not a closed system since an act of inhalation results in the valve 460 becoming unseated from the atmospheric vent port 450, thereby letting air from the atmosphere to enter the holding chamber 420. This will result in mixing of the aerosolized particles (medication) with the atmospheric air entering through the vent port 450, which consequently results in a reduction in the concentration of the medication.

When it is desired to use the apparatus as a means for delivering medication over time from a nebulizer, the cap 219 is removed from the port 218 and a nebulizer is connected thereto for delivering aerosolized particles into the apparatus and in particular into the main conduit 410 and into the holding chamber 420. Before the patient inhales, the aerosolized particles are delivered into the holding chamber 420 since the second valve (inhalation valve) 480 remains closed and the first valve 470 remains open to permit the patient to exhale. As the patient inhales to capture and breathe in the aerosolized particles, the first valve 470 closes, the second valve 480 opens to permit passage of the aerosolized particles from the holding chamber 420 into the main conduit 410 and at the same time, the valve 460 unseats from the vent port (seat) 450 to let in some air from the atmosphere to permit the patient to be able to inhale and draw the aerosolized particles from the holding chamber 420 and through the main conduit body 410.

While the above valve assemblies have been described as being flap valves or the like, it will be appreciated that any number of other valve types can be used so long as they are suitable for the intended use and move from open to closed positions and vice versa upon the occurrence of an event, such as inhalation or exhalation. When the valve is a flap valve, the valve seats is a circumferential surface of landing that surrounds an opening or port that is completely occluded by the valve when the valve is in the closed position. The valve can thus have a circular structure that is attached to the valve seat at a point. A majority of the flap valve is not attached to any structure and therefore is free to move both away from and towards the valve seat. On inhalation, the free edge of the inhalation flap valve, e.g., valve 480 of FIG. 14, moves away from the respective valve seat to permit the aerosolized particles to move from the holding chamber 420 through the opening in this valve seat. On exhalation, the opposite occurs in that the free edge of the inhalation flap valve 480 moves toward the valve seat and closes the opening to prevent any flow of gas exhaled by the patient from entering into the holding chamber 420, thereby avoiding re-breathing of carbon dioxide by the patient on the next inhalation. The exhalation flap valve, e.g., valve 470, can have a similar construction in that it can be attached to its respective valve seat at a point, while most of the flap valve body is free to move relative to the valve seat. The free edge of this valve presses against the valve seat on inhalation and completely occludes the opening to prevent any room air entrainment, i.e., not allowing the air from the atmosphere to enter into the mouthpiece or the first chamber 110 on inhalation. On exhalation, the free edge of the flap valve moves away from the valve seat to permit the air exhaled by the patient to escape into the atmosphere from the opening in the fourth conduit member 160/mouthpiece/facemask.

Optionally, the device 400 can include a supplemental fluid port 490 that is formed in the main body 410 between the valve assembly 480 and the end 412. The port 490 is thus an inlet that can include a boss or the like to permit attachment of a conduit thereto. The port 490 thus defines an entrance into the main conduit body 410 and is positioned such that when the valve assembly (inhalation) 480 is open and the valve assembly (exhalation) 470 is closed, the fluid (typically a gas, such as oxygen), as when the patient inhales, the fluid flows into the main conduit body 410 and then into the patient. This fluid (gas) that enters the port 490 merely supplements the main source of gas (either the MDI 170 or the nebulizer, as well as atmospheric air that enters the valve port 450) and also permits the physician to vary the concentration of gas as by diluting the gas in the holding chamber 420 with gas entering the port 490. When not in use, the port 490 is merely capped with a cap 492. When the patient exhales and the valve assembly 470 opens and the valve assembly 480 closes, the gas entering the port 490 is merely vented out through the valve assembly 470.

In an alternative embodiment, the inhalation valve and/or the exhalation valve can be constructed so that instead of being a generally circular shaped valve member, the valve can be cut into two parts, namely a first hemispherical shaped part and a second hemispherical shaped part. The first hemispherical shaped part is attached to the valve seat at one location and the second hemispherical shaped part is attached to the valve seat at another location, such as a location that is 180 degrees from the first location. The two free edges of the two hemispherical shaped valve parts meet at a center line such that there is no gap between the two free edges. On inhalation, the two free edges of the inhalation flap valve move away from the valve seat for the aerosol particles to move from the first chamber or the holding chamber to the patient through the opening in the respective valve seat. On exhalation, the free edges of the inhalation flap valve move towards the flap valve seat and close the opening to prevent any flow of gas exhaled by the patient from entering into the first chamber/holding chamber, thereby avoiding re-breathing of carbon dioxide on the next inhalation. In the exhalation valve assembly, the two free edges of the flap valve press against the flap valve seat on inhalation and completely occlude the opening to prevent any room air entrainment, i.e., not allowing the air from the atmosphere to enter into the mouthpiece or the first chamber/ holding chamber on inhalation. On exhalation, the free edge of the two valve parts move away from the valve seat for the air exhaled by the patient to escape into the atmosphere from the opening in the fourth conduit member 160 (outlet tube/ mouthpiece/facemask).

Figure 10:
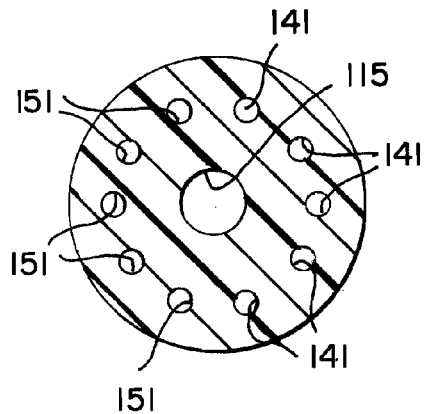
FIG. 10 is a cross-sectional view of an inlet end of one exemplary holding chamber.

FIG. 10 is a cross-sectional view of an inlet end of one exemplary first chamber (MDI chamber) that has a different arrangement compared to the arrangement in FIG. 1. More specifically and according to this alternative embodiment, the inlet end has a circular cross-section with an outer circumferential peripheral edge. There is a central opening 115 in the inlet end to receive and sealingly mate with the first conduit member 130 (FIG. 1) and according to this embodiment, the two peripheral second and third conduit members 140, 150 (FIG. 1) that are orientated at the 3 and 9 o'clock positions in the embodiment of FIG. 1 are replaced with a plurality of radial micro-sized openings that define fluid entrances into the interior of the first chamber 110. More specifically and at the inlet end of the first chamber 110, the second conduit 140 is split into a first set of micro-sized (micrometric) conduits that mate with a first set of micro-sized openings 141 formed at the inlet end; and similarly, the third conduit 150 is split into a second set of micro-sized (micrometric) conduits that mate with a second set of micro-sized openings 151. As shown in FIG. 10, the first set of openings 141 are radial openings formed on hemisphere of the inlet end, while the second set of openings 151 are radial openings formed on the opposite hemisphere of the inlet end. The number of micro-openings in each half is not critical and therefore, the illustrated amount of 5 micro-sized openings in each half of the inlet end is merely exemplary in nature and not limiting. The aerosolized particles from the second (nebulizer) chamber 120 enter into the first chamber 110 either through the central first conduit 115 or through the inlet ends of the second and third conduits 140, 150. After entering the second and third conduits 140, 150, the aerosol particles enter into the first chamber 110 through the first and second set of micrometric openings 141, 151.

Figure 11:
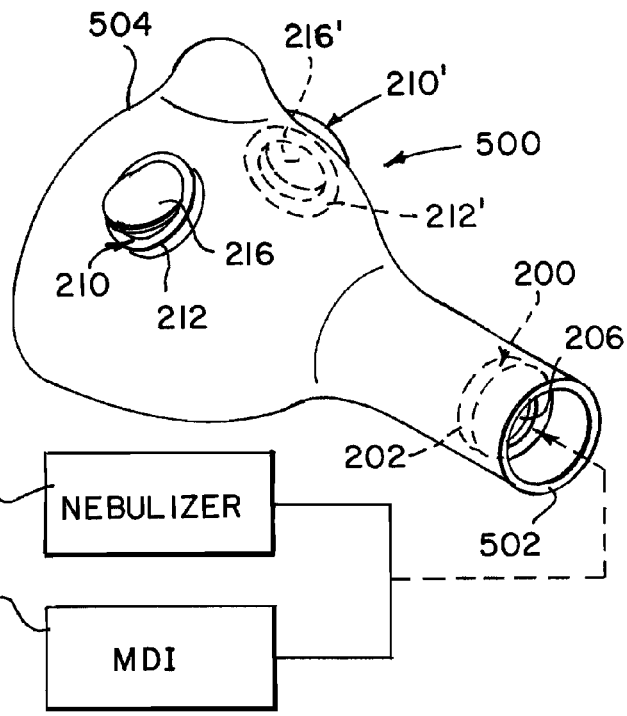
FIG. 11 is a side perspective view of a facemask having a valve mechanism incorporated therein and intended to mate with a holding chamber for delivering the aerosol particles.

While in FIG. 1, the two valve assemblies 200, 210 are located within the fourth conduit member 160, there are other possible designs in which these two valve assemblies 200, 210 are located in different locations. More specifically, FIG. 11 shows an alternative embodiment in which a facemask 500 is generally illustrated. The facemask 500 is connected at a first end 502 to the first chamber 110 (holding chamber) and is fitted at the opposite second end 504 to the patient for inhalation of the aerosol medication generated either by the nebulizer 290 or the MDI 170 as demonstrated in one of the previously described embodiments, such as the embodiment of FIG. 1. The facemask 500 is intended to be attached to the outlet end 164 of the fourth conduit member 160 of FIG. 1. The first end 502 of the facemask 500 serves as an inlet end, while the second end 504 of the facemask 500 serves as an outlet end. In this embodiment, the exhalation, inhalation valve assemblies 210, 200 are incorporated into the construction of the facemask 500 as opposed to being disposed in the fourth conduit member 160.

More specifically, the exhalation and inhalation valve assemblies 210, 200 are incorporated into the facemask 500 between the inlet end 502 and the outlet end 504. The actual construction of the respective valve can be the same as in FIG. 1 in that the inhalation valve assembly 200 includes the valve seat 202 and the flap valve 206 and the exhalation valve assembly 210 includes the valve seat 212 and the flap valve 216. On inhalation, the inhalation valve 206 moves away from its respective seat 202 for the aerosol particles to move from the first chamber 110 (holding chamber) to the patient through the opening in the valve seat 202 associated with the mouthpiece. On exhalation, the inhalation flap valve 206 moves toward its respective seat 202 and closes the opening formed therethrough to prevent any flow of gas exhaled by the patient from entering into the first chamber 110 (holding chamber). The flap valve 216 seats against the seat 212 on inhalation and completely occludes the opening formed in the seat 212 to preclude any room air entrainment.

Similar to the earlier embodiments and opposite to the valve actions associated with inhalation, on exhalation, the flap valve 216 moves away from the seat 212 for the air exhaled by the patient to be escape into the atmosphere. FIG. 11 illustrates the facemask 500 having an additional exhalation valve assembly 210' including flap valve 216' and valve seat 212', which functions in the same manner as exhalation valve assembly 210.

Figure 12:
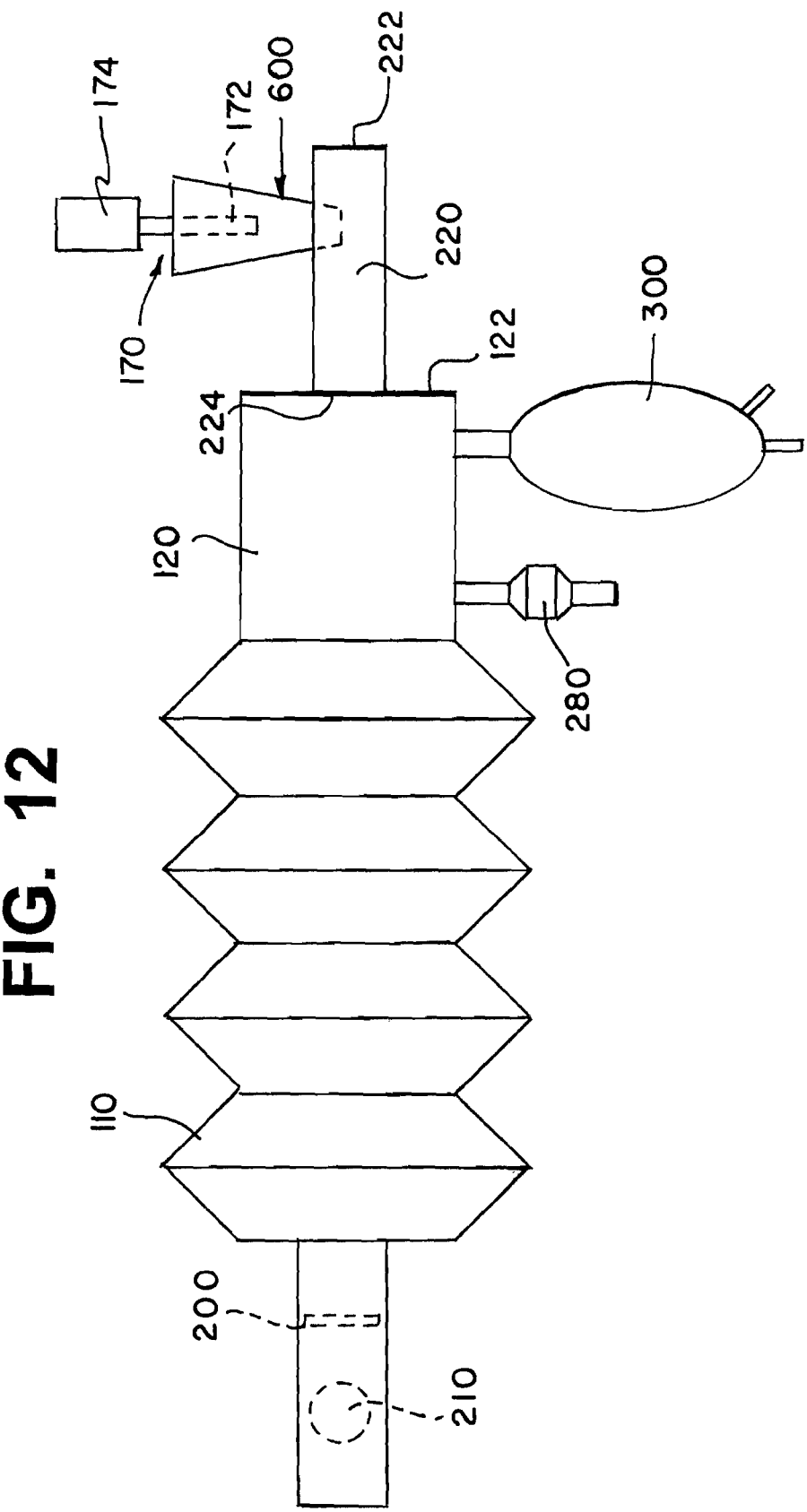
FIG. 12 is a side elevation view of an aerosol inhalation system according to a fifth embodiment and having a universal MDI actuator incorporated therein.

FIG. 12 shows yet another embodiment of the present invention which is similar to the embodiment illustrated in FIG. 3 with a modification. More specifically and according to this embodiment, the apparatus includes the first chamber (MDI chamber) 110, the second chamber (nebulizer chamber) 120, and the fourth and fifth conduit members 210, 220, that are fluidly attached to the first and second chambers 110, 120, respectively. According to this embodiment, a universal actuator 500 is disposed between the inlet end 222 and the outlet end 224 of the fifth conduit member 220 that is located at the inlet end 122 of the nebulizer chamber 120. The universal actuator 600 is configured so that the nozzle of any commercially available MDI canister can be attached to the universal actuator 600 and medication delivered by actuation of the MDI 170. The inlet end 222 of the fifth conduit member 220 at the inlet end 122 of the nebulizer chamber 120 can be attached to one or more gas sources to yield a mixture of gas(es) with desired density, oxygen concentration, viscosity, and humidity to improve the delivery of aerosol particles as well as deliver a fixed concentration of oxygen to a hypoxemic patient. Alternatively, the universal actuator 600 can be provided and the nozzle 172 of the canister (which can be any number of different commercially available units) can be attached to and the actuator 174. The actuator has the opening or aperture as seen in FIG. 1. On actuation of the canister, the medication aerosol particles are generated through the opening of the actuator.

As in the embodiment of FIG. 3, the apparatus according to this embodiment includes first and second chambers 110, 120 that are sealingly attached to one another, as by using an adhesive material, fusing, or otherwise bonding.

In yet another embodiment, a concentric tube can be disposed about the fifth conduit member 220, with the universal actuator 500 being integral thereto and passing through the concentric tube and into fluid communication with the fifth conduit member 220. When this outer concentric tube is present about the fifth conduit member 220, one or more vent openings can be formed in the inlet end 122 of the second (nebulizer) chamber 120. Since the vent openings fluidly communicate with the interior of the open ended concentric tube, gas(es) from the atmosphere or another outside gas source can flow into the nebulizer chamber 120 from the open end of the concentric tube through the vent openings. The flow is only peripheral to the flow through the fifth conduit member 220 and there is no central flow as the inlet end 222 of the fifth conduit member 220 is closed as by capping this end 222.

It will be appreciated that the concentric tube surrounding the fifth conduit member 220 can be a rigid structure or it can have a variable length as by being a collapsible/expandable member, such as the bellows/accordion type structures shown hereinbefore. In addition, the concentric structure does not have to be completely open-ended at its inlet end but instead, the concentric structure can include an inlet end wall structure with an opening that receives a conduit member, such as a tube that can serve as a conduit to deliver air or an external gas; however, the conduit can be capped.

In embodiments where atmospheric air is permitted to enter the second chamber 120, the apparatus is not a closed system, as in many of the previously described embodiments, but instead is an open system and therefore, the concentration of the medication delivered to the patient does not remain fixed.

Each of the above described devices/accessories can be used in conventional inhalation equipment settings and thus can be used with either a nebulizer, an MDI, or both and they overcome the deficiencies that are associated with the prior art aerosol inhalation systems.

Having described embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims.

What is claimed is:

1. An aerosol inhalation system comprising:
 a first conduit member for delivering medication in the form of aerosol particles to a patient;
 a first holding chamber for holding the aerosol particles prior to deliver to the first conduit member;
 a valve mechanism associated with the first conduit member and including a first valve assembly and a second valve assembly, the first valve assembly being positionable between an open position and a closed position where the fluid is prevented from flowing between the first holding chamber and the first conduit member as when the patient exhales, the first valve assembly assuming the open position as the patient inhales, the second valve assembly being positionable between an open position where the first conduit member is vented to atmosphere as when the patient exhales and a closed position when the patient inhales and the first valve assembly opens, and
 at least one device in fluid communication with the first holding chamber for producing the aerosol particles;
 wherein the aerosol inhalation apparatus is a closed system and is therefore capable of delivering a fixed concentration of the medication to the patient due to the second valve assembly being closed when the patient inhales and the medication is delivered to the patient, wherein the first holding chamber has a variable interior volume and is defined by a body that is collapsible and expandable in length so as to vary the interior volume.

2. The system of claim 1, wherein the first conduit member comprises a hollow conduit body that carries the aerosol particles from the first holding chamber when the patient inhales for purpose of delivering the medication into the patient and carries discharged gases from the patient when the patient exhales for purpose of venting these gases to atmosphere.

3. The system of claim 1, wherein the first holding chamber has a variable length such that when the length of the first holding chamber is at a minimum, the interior volume thereof is at a minimum and when the length of the first holding chamber is at a maximum, the interior volume thereof is at a maximum.

4. The system of claim 1, wherein the body comprises a bellows type structure.

5. The system of claim 1, wherein the body is formed of a corrugated plastic material.

6. The system of claim 1, wherein the body includes a reinforcing member to ensure integrity of the body as the body either collapses or expands along its length.

7. The system of claim 6, wherein the reinforcing member comprises a coil structure.

8. The system of claim 1, wherein the first valve assembly is disposed proximate an interface between the first conduit member and the first holding chamber and includes a first valve and a first valve seat having an opening extending therethrough for permitting selective flow of the aerosol particles when the first valve is open relative to the first valve seat, the first valve sealingly seating against the first valve seat in the closed position.

9. The system of claim 1, wherein the second valve assembly is disposed between the first valve assembly and an open outlet end of the first conduit member, the second valve assembly including a second valve and a second valve seat having an opening extending therethrough for permitting the discharged gases to flow into atmosphere when the second valve is open relative to the second valve seat, the second valve sealingly seating against the second valve seat in the closed position.

10. The system according to claim 8, wherein the first valve is a flap valve.

11. The system according to claim 9, wherein the second valve is a flap valve.

12. The system according to claim 1, wherein the at least one device comprises one of a metered dose inhaler and a nebulizer.

13. The system according to claim 12, further including: a second holding chamber in fluid communication with the first holding chamber and including a first port for attachment to the at least one device.

14. The system according to claim 13, wherein when the at least one device comprises a metered dose inhaler (MDI), the first holding chamber includes an MDI port that permits fluid attachment to the MDI; and wherein the second holding chamber is fluidly connected to the first holding chamber by means of one or more collapsible/expandable linking conduits that communicate with an interior of both the first and second holding chambers, wherein when the linking conduit is in an expandable position, the at least one device in the form of a metered dose inhaler (MDI) can be disposed between the first and second chambers and placed in fluid communication with the first holding chamber, while still permitting a nebulizer to be fluidly attached to the first port of the second holding chamber for delivering aerosol particles into an interior of the second holding chamber and through the linking conduit to the first holding chamber that is fluidly connected thereto.

15. The system according to claim 14, wherein the second holding chamber includes a second port with a reservoir bag fluidly attached to the second port, the linking conduit having a variable length.

16. The system according to claim 13, wherein the second holding chamber has a variable interior volume.

17. The system of claim 16, wherein the second holding chamber is defined by a body that has a variable length such that when the length of the first holding chamber is at a minimum, the interior volume thereof is at a minimum and when the length of the first holding chamber is at a maximum, the interior volume thereof is at a maximum.

18. The system of claim 17, wherein the body defining the second holding chamber comprises a bellows type structure.

19. The system of claim 17, wherein apparatus has two or more settings correlated to a weight of the patient, wherein for each selling, a body defining the first holding chamber is in one of a compressed state or an expanded state and the body defining the second holding chamber is in one of a compressed state or an expanded state.

20. The system of claim 19, wherein the two or more settings comprise at least a child selling and an adult setting, wherein the first holding chamber is at least partially expanded in the child state and the second holding chamber is fully compressed in the child state.

21. The system of claim 20, wherein the first holding chamber is frilly expanded and the second holding chamber is at least partially expanded in the adult setting.

22. The system of claim 19, wherein each of the bodies defining the first and second holding chambers, respectively, includes a lock mechanism for locking the body of the respective holding chamber in a position where an interior volume thereof is fixed to a predetermined value.

23. The system of claim 14, wherein each linking conduit branches into a plurality of inlet conduits that are received in corresponding radial openings formed in an end connector at the inlet end of the first holding chamber so as to more uniformly disperse the aerosol particles from the second holding chamber into the first holding chamber.

24. An accessory for an aerosol inhalation system comprising:
   a main conduit body having an open first and an opposing open second end;
   a first port formed as part of the main conduit body;
   a second port formed as part of the main conduit body; a first holding chamber operably coupled to second end of the main conduit body and in selective fluid communication with the first end of the main conduit body; and
   a valve mechanism associated with the main conduit body and including a first valve assembly and a second valve assembly, the first valve assembly being positionable between an open position and a closed position where the fluid is prevented from flowing between the first holding chamber and the first port when the patient exhales, the first valve assembly assuming the open position as the patient inhales, the second valve assembly being disposed in the first port and being positionable between an open position where a portion of main conduit body is vented to atmosphere, when the patient exhales, and a closed position when the patient inhales and the first valve assembly opens;
   wherein the first holding chamber has a variable volume and includes a main connector port to permit attachment of at least one device for generating and delivering the aerosol particles to the first holding chamber, the first holding chamber having an air vent with a third valve assembly that opens when the patient inhales and closes when the patient exhales to assist in flow of the aerosol particles from the first holding chamber into the main conduit body;
   wherein a body defining the first holding chamber has a variable length such that when the length of the first holding chamber is at a minimum, the interior volume thereof is at a minimum and when the length of the first holding chamber is at a maximum, the interior volume thereof is at a maximum, wherein the body comprises a bellows type structure.

25. The accessory of claim 24, wherein the first valve assembly is disposed between the first and second ports and includes a first flap valve such that when the first flap valve assumes the closed position, fluid is prevented from flowing within the main conduit body between the first and second ports.

26. The accessory of claim 24, further including a nebulizer fluidly sealingly attached to the second port.

27. The accessory of claim 24, wherein the second valve assembly includes a flap valve disposed in the first port and opening and the third valve assembly includes a flap valve operably mounted to an interior wall of the holding chamber such that in the closed position, the flap valve covers the air vent formed in the interior wall.

28. The accessory of claim 24, further including an MDI connector port formed as part of the body defining the first holding chamber and being in fluid communication therewith.

29. An aerosol inhalation system comprising:
   a first conduit member for delivering medication in the form of aerosol particles to a patient;
   a first holding chamber for holding the aerosol particles prior to deliver to the first conduit member, wherein the first holding chamber is defined by a body having a bellows shape that is collapsible and expandable in length so as to vary an interior volume of the first holding chamber;
   a valve mechanism associated with the first conduit member and including a first valve assembly and a second valve assembly, the first valve assembly being positionable between an open position and a closed position where the fluid is prevented from flowing between the first holding chamber and the first conduit member as when the patient exhales, the first valve assembly assuming the open position as the patient inhales, the second valve assembly being positionable between an open position where the first conduit member is vented to atmosphere as when the patient exhales and a closed position when the patient inhales and the first valve assembly opens, and
   at least one device in fluid communication with the first holding chamber for producing the aerosol particles;
   wherein the aerosol inhalation apparatus is a closed system and is therefore capable of delivering a fixed concentration of the medication to the patient due to the second valve assembly being closed when the patient inhales and the medication is delivered to the patient.

30. An aerosol inhalation system comprising:
   a first conduit member for delivering medication in the form of aerosol particles to a patient;
   a first holding chamber for holding the aerosol particles prior to deliver to the first conduit member, wherein the first holding chamber includes an end conduit for connection to an external device;
   a valve mechanism associated with the first conduit member and including a first valve assembly and a second valve assembly, the first valve assembly being positionable between an open position and a closed position where the fluid is prevented from flowing between the first holding chamber and the first conduit member as when the patient exhales, the first valve assembly assuming the open position as the patient inhales, the second valve assembly being positionable between an open position where the first conduit member is vented to atmosphere as when the patient exhales and a closed position when the patient inhales and the first valve assembly opens;
   a second holding chamber that is fluidly connected to the first holding chamber by means of a pair of conduit members, each conduit member being defined by a body that is collapsible/expandable along its length, wherein the end conduit is disposed between the conduit members that fluidly attach the second holding chamber to the first holding chamber to permit receipt of the external device;
   at least one device in fluid communication with the second holding chamber for producing the aerosol particles;
   wherein the aerosol inhalation apparatus is a closed system and is therefore capable of delivering a fixed concentration of the medication to the patient due to the second valve assembly being closed when the patient inhales and the medication is delivered to the patient.

* * * * *